US006627758B2

(12) United States Patent
Grotjahn

(10) Patent No.: US 6,627,758 B2
(45) Date of Patent: Sep. 30, 2003

(54) COMPOSITIONS AND METHODS FOR HYDRATION OF TERMINAL ALKYNES

(75) Inventor: Douglas Bryan Grotjahn, San Diego, CA (US)

(73) Assignee: San Diego State University Foundation, San Diego, CA (US)

( * ) Notice: Subject to any disclaimer, the term of this patent is extended or adjusted under 35 U.S.C. 154(b) by 0 days.

(21) Appl. No.: 09/785,911

(22) Filed: Feb. 16, 2001

(65) Prior Publication Data

US 2002/0115860 A1 Aug. 22, 2002

Related U.S. Application Data

(63) Continuation-in-part of application No. 09/273,082, filed on Mar. 19, 1999.

(51) Int. Cl.[7] ........................ C07F 17/02; C07D 403/12
(52) U.S. Cl. ................ 548/101; 548/312.7; 548/324.5; 548/325.1; 548/326.1; 548/335.1; 548/111
(58) Field of Search ................................ 548/101, 105, 548/106, 111, 312.7, 324.5, 325.1, 326.1, 335.1

(56) References Cited

U.S. PATENT DOCUMENTS

| 5,159,099 A | 10/1992 | Romano et al. |
| 5,206,409 A | 4/1993 | Romano et al. |
| 5,597,942 A | 1/1997 | Pohl et al. |
| 5,599,994 A | 2/1997 | Pal et al. |
| 5,621,155 A | 4/1997 | Benham et al. |
| 5,624,969 A | 4/1997 | Seifert et al. |
| 5,663,064 A | 9/1997 | Burke et al. |
| 5,684,092 A | 11/1997 | Seifert et al. |
| 5,684,212 A | 11/1997 | Patton et al. |
| 5,705,078 A | 1/1998 | Kurek et al. |
| 5,719,273 A | 2/1998 | Tu et al. |
| 5,723,663 A | 3/1998 | Jackson et al. |
| 5,739,022 A | 4/1998 | Burstyn et al. |
| 5,741,955 A | 4/1998 | Beatty |
| 5,760,275 A | 6/1998 | Lassila |
| 5,763,652 A | 6/1998 | Kawabe et al. |
| 5,763,716 A | 6/1998 | Benham et al. |
| 5,817,635 A | 10/1998 | Eckstein et al. |
| 5,817,872 A | 10/1998 | Honda et al. |
| 5,820,840 A | 10/1998 | Horn Feja et al. |
| 5,821,553 A | 10/1998 | Evans et al. |
| 5,837,855 A | 11/1998 | Chowrira et al. |
| 5,840,500 A | 11/1998 | Pei et al. |

FOREIGN PATENT DOCUMENTS

JP       11319576       11/1999

OTHER PUBLICATIONS

Antinolo, A. et al. : New functionalized bis(pyrazol–1–yl)methane ligands. J.Chem. Soc. Dalton Trans. vol. 22, pp. 3737–3743, 1998.*
Lopez–Garzon, R. et al. : Syntheis and structural studies on Imidazole metal complexes. Polyhedron, vol. 12, pp. 507–512, 1993.*
Goodgame, D.M. et al. : Metal complexes as radiosensitizers. Polyhedron, vol. 11, pp. 2507–2515, 1992.*
Deters et al, Inorganic Chimica Acta, 269 (1998) 117–124.
Kovari et al, Chem. Ber. (1994) 127, 2151–2157.
Meyer et al, Chem. Ber. (1997) 130, 605–613.
Katritzky et al, J. Org. Chem. (1988) 53, 5685–5689.
Begtrup, Acta Chemica Scandinavica 46 (1992) 972–980.
Rheingold et al, Inorg. Chem. (1993) 32, 3471–3477.
Singh et al, Inorg. Chem. (1998) 37, 1073–1079.
Konrad et al, J. Chem. Soc. Dalton Trans. (1998) 199–205.
Meyer et al., J. Chem. Soc., Dalton Trans. (1998) 1181–1186.
Cheng et al, J. Am. Chem. Soc. (1998) 120, 11018–11019.
Zadykowicz et al., J. Org. Chem. (1998) 63, 235–240.
Krooglyak et al., Inorg. Chem. (1996) 35, 4804–4806.
Comprehensive Coordination Chemistry, 2, 1987, p. 310.
Kovari et al, J. Am. Chem. Soc. (1996) 118, 12704–12709.
Zhu et al., J. Am. Chem. Soc. (1993) 115, 4566–4570.
Parac et al., J. Am. Chem. Soc. (1996) 118, 5946–5951.
Kaminskaia et al, Inorg. Chem. (1998) 37, 4302–4312.
Redmore et al, Inorg. Chem. (1997), 36, 4743–4748.
Van et al, Abstract of II Symposium International: Investigation Quimica En La Frontera Dec. 9, 1998.
Satake et al, J. Am. Chem. Soc. (1998), 120, 10391–10396.
Schenck et al, Inorg. Chem. (1985) 24, 2334–2337.
Meyer et al, Chem. Ber./ Recueil (1997) 130, 1441.
Jones, R.G., J. Am. Chem. Soc. (1949) 3994–4000.
M.T. Alonso et al, Journal of Organometallic Chemistry, 430 (1992) 335–347.
Cano, M. et al: 3–[4–phenoxyphenyl]pyrazole (Hpz) and 3–[4–butoxyphenyl]pyrazole (Hpz) in rhodium chemistry. J. Organomettal. Chem. vol. 534, pp. 159–172.
Tokunaga et al., Angew. Chem. Int. Ed. (1998), 37, No. 20 pp. 2867–2869.

* cited by examiner

*Primary Examiner*—Charanjit S. Aulakh
(74) *Attorney, Agent, or Firm*—Stout, Uxa, Buyan & Mullins, LLP; Frank J. Uxa

(57) ABSTRACT

Compositions and methods are described for hydrating terminal alkynes catalytically in anti-Markovnikov fashion. The compositions comprise a transition metal complex including at least one organic ligand having at least two heteroatoms, wherein the heteroatoms are directly bonded or located one atom away. Preferably, at least one of the heteroatoms is nitrogen, which is typically provided as part of a heterocyclic ring. Other preferred heteroatoms include S, P, N, As or Se. A particularly preferred catalyst employs a P-linked imidazole ligand bound to Ru. Such complexes have a controlled adaptable proton transfer ability and/or a hydrogen bonding ability making them particularly useful as chemical reaction facilitators.

17 Claims, No Drawings

COMPOSITIONS AND METHODS FOR HYDRATION OF TERMINAL ALKYNES

REFERENCE TO RELATED APPLICATION

The present application is a continuation-in-part of U.S. Ser. No. 09/273,082, filed Mar. 19, 1999.

BACKGROUND OF THE INVENTION

The present invention relates to ligands, transition metal complexes including the ligands, and methods of using the ligands and transition metal complexes. More particularly, the invention relates to ligands including first and second heteroatoms, transition metal complexes of such ligands, and methods of using the ligands and complexes, for example, to facilitate chemical reactions, such as hydration of terminal alkynes.

Medicinal chemists and biochemists want to know how amino acids are arranged in proteins, so that they can better understand the correlation between structures and the functions of drugs. One of the techniques used to accomplish the task of protein structure determination requires the breaking of amide bonds to liberate the amino acids. However, at physiological temperatures and pH 9, it takes an impractical length of time, for example, 168 years, to break half the amide bonds in a sample. In contrast, organisms found in nature have remarkably efficient systems to make and break amide bonds. Scientists have used natural enzymes such as carboxypeptidase to do the task of amide bond cleavage.

In some cases, it is believed that the crucial step involves proton transfer between imidazole, a carboxylate, and the amide undergoing hydrolysis, while other enzymatic systems involve a metal-catalyzed amide bond cleavage such as that seen in the zinc(II)-metalloprotease. However, existing enzymatic systems can be very complicated and sometimes difficult to handle due to their sensitivity to temperature and pH.

Amide hydrolysis has been catalyzed not only by enzymes, but also by acids, bases, and metal ions. These systems take advantage of one or more possible factors, which facilitate amide bond cleavage. First, the amide bond cleaving reagent or catalyst could act as a proton transfer reagent, which can be an important factor in amide bond hydrolysis. Secondly, a metal may catalyze or mediate amide hydrolysis by acting as a Lewis acid through O-complexation, delivery of a metal-coordinated hydroxide or a combination of the latter two processes.

Considerable work has been directed toward studying the amide hydrolysis reaction and the development of reagents that assist amide hydrolysis. Some work toward the development of an amide hydrolysis catalyst has been published by Kostic. For example, Kostic and coworkers have found that a palladium(II) complex can accomplish the hydrolysis of a number of dipeptides, but with only a modest 4 catalytic turnovers.

It would be advantageous to provide reaction facilitators, e.g., catalysts, promoters and the like, that mimic enzymatic systems in their hydrogen-bonding and/or proton transfer abilities, but are robust, simple to handle, and have useful reactor facilitation.

Industrial hydrolysis of acrylonitrile is used to make acrylic acid which, in turn, can be converted to a variety of esters such as methyl, ethyl, butyl, and 2-ethylhexyl acrylates. The acrylates can then be used as comonomers with methyl methacrylate and/or vinyl acetate to give polymers for water-based paints, among other products. A number of industrial methods exist for obtaining acrylic acids from nitriles and one of the more economical methods is the direct hydrolysis of the acrylonitrile to the acrylic acid. However, this synthetic route involves the use of a stoichiometric amount of sulfuric acid to produce the acrylamide sulfate, which is then treated with an alcohol to give the acrylic ester. It would be advantageous to provide a direct route from the acrylonitrile and alcohol to yield the desired acrylate without the need to use and then neutralize a strong acid.

As petroleum resources dwindle and the need to control the emissions of carbon dioxide into the environment increases, use of carbon dioxide as a feedstock becomes more desirable. It would be advantageous to provide materials useful to facilitate carbon dioxide conversion, for example, to carbonates, carbamates and ureas.

A further example of environmentally desirable methods of conducting organic synthesis involves the use of water in the oxidation of unsaturated hydrocarbons. For example, the metal-catalyzed hydration of alkynes is an important route to carbonyl compounds. The use of water in such syntheses has the additional advantages of ease of use, safety, and economic savings. Most metal-catalyzed hydrations of 1-alkynes follow Markovnikov addition to give ketones. Recently, anti-Markovnikov addition has been reported, which gives aldehydes and a small amount of ketones [Tokunaga, M., et al. *Angew. Chem. Int. Ed.*, 37(20), 2867–2869 (1998); JP 11319576].

It is desirable to identify and exploit the novel cooperativities afforded by metal ions and suitable organic ligands in additional industrial processes, for example, in the hydration of terminal alkynes. It is preferred that such reactions be catalytic in nature so that the organometallic complex is not consumed during the reaction.

SUMMARY OF INVENTION

New organic ligands, transition metal complexes including such ligands and methods for using the ligands and complexes have been discovered. The present ligands and transition metal complexes can be produced using relatively straightforward synthetic chemistry techniques. Moreover, the structures of the present ligands and metal complexes can be effectively selected or even controlled, for example, in terms of proton transfer ability and/or hydrogen bonding ability, thereby providing ligands and complexes with properties effective to facilitate one or more chemical reactions. Thus, the present metal complexes can be effectively used to facilitate, for example, catalyze, promote, and the like, various chemical reactions, such as hydrolysis, alcoholysis, aminolysis, carbon dioxide conversion, and hydration reactions, which provide useful benefits.

In one broad aspect of the present invention, compositions are provided which comprise at least one organic ligand and a transition metal moiety partially complexed by the organic ligand.

The present organic ligands, many of which themselves are novel and within the scope of the invention, include a first heteroatom and a second heteroatom. The first and second heteroatoms are covalently bonded to each other or separated from the other by at least one atom, for example, a carbon atom. Whenever the present organic ligands are complexed to a transition metal moiety, one or both of the first and second heteroatoms is/are covalently bonded to the transition metal moiety. In particular, each of the first and second heteroatoms presents a lone pair of electrons that can be free (unbonded), protonated, occasionally or temporarily bonded to an aforementioned transition metal moiety, e.g., through a coordinate covalent bond, or hydrogen bonded to a second molecule, e.g., water. It is this variability in functionality that affords the desired cooperativity sought in a ligand of the invention, especially whenever catalytic activity is desired.

In one embodiment of the invention, a composition includes an organic ligand having the following structure:

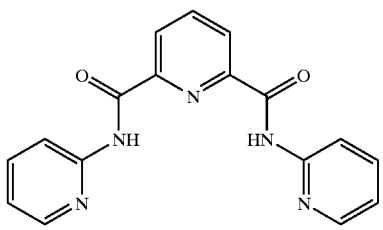

In this molecule, one or more of the pyridyl N atoms binds to a transition metal moiety, for example, containing ruthenium.

In a further aspect of the invention, an organic compound includes at least two different types of heteroatoms selected from among N, P, and S, and further includes at least one substituted or unsubstituted heterocycle selected from imidazole, pyrazole, and pyridine groups. In this molecule, the at least two different types of heteroatoms are separated from each other by at least one atom, e.g., a carbon atom. The heteroatoms are preferably selected so that at least one is capable of binding to a transition metal and another has a binding affinity for water through a hydrogen bond.

In another preferred embodiment, a ligand of the invention includes an N-heterocycle covalently linked to a P-atom. A particularly preferred ligand in this regard is a P-linked imidazole having the formula shown below:

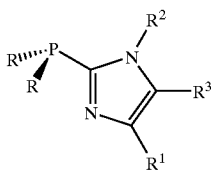

Whenever an aforementioned P-linked imidazole is coordinated to Ru in a transition metal complex for use in the anti-Markovnikov hydration of 1-alkynes, it is preferred that $R^1$, $R^2$, and $R^3$ are independently selected from hydrogen or alkyl, and R is alkyl or aryl. Most preferably, the ligand has $R^1$=t-butyl, $R^2$=methyl, $R^3$=H, and R=phenyl.

The present organic ligands can be very effectively structured and adapted to control the proton transfer ability and/or hydrogen bonding ability of the transition metal complex of which the ligand is a part. In other words, the present ligands can be selected to obtain the desired degree of proton transfer ability and/or hydrogen bonding ability so that the resulting transition metal complex is highly effective in performing a desired chemical transformation, for example, hydrolysis, alcoholysis, aminolysis, carbon dioxide conversion, and addition of water, alcohols, ammonia or amines to alkenes and alkynes. Such reactions are typically performed by a cooperativity between one heteroatom binding the transition metal and a second heteroatom of the ligand performing H atom transfers with one or more reactants.

In an additional broad aspect of the present invention, methods for reacting alkenes or alkynes with water, alcohols, ammonia or amines are provided. Such methods comprise contacting the reactants in the presence of a transition metal complex of the invention in an amount effective to facilitate the desired reaction to one or more desired products. The contacting occurs at effective reaction conditions. In a particularly preferred method, terminal alkynes are catalytically converted to aldehydes with high selectivities at or near neutral pH.

Each feature and combination of two or more features described herein are included within the scope of the present invention provided that any two features of any such combination are not mutually inconsistent or incompatible.

These and other aspects and advantages of the present invention are set forth in the following detailed description, examples and claims.

DETAILED DESCRIPTION

In one aspect, the present invention is directed to organic ligands including a first heteroatom and a second heteroatom directly bonded to the first heteroatom or located one carbon atom away from the first heteroatom. Exemplary heteroatoms include nitrogen atoms (N), oxygen atoms (O), sulfur atoms (S) and phosphorus atoms (P). At least one of the first and second heteroatoms is preferably nitrogen.

In one embodiment, an organic ligand of the invention includes at least one nitrogen heterocycle, for example, a substituted or unsubstituted six- or five-membered heterocycle. Included among the six-member rings are substituted or unsubstituted pyridine, pyridazine, pyrimidine, pyrazine, triazine and tetrazine rings. Among the five-member rings are substituted or unsubstituted pyrazole, benzopyrazole, imidazole, benzimidazole and triazole rings.

In a preferred aspect, a ligand of the invention is neutral in charge and joins two or more heteroatoms separated by at least one intervening atom. At least one of the heteroatoms binds to a transition metal moiety with another heteroatom substantially free to interact with one or more reactant molecules, e.g., water or alkyne. Such ligands are conveniently provided by covalently linking one or more heterocyclic ring(s) to one or more heteroatom(s) outside the ring. The heteroatom(s) outside the first heterocycle can also be present in a ring structure, but need not be. Judicious selection of heteroatoms outside a ring structure can afford an economical and straightforward synthesis of the ligand.

In a particularly preferred aspect of the invention, a ligand covalently links an N heterocycle with a heteroatom different from N, e.g., P or S, outside the heterocyclic ring.

Representative organic ligands in accordance with the present invention are shown by the following structures, wherein "n" is an integer independently selected from one or two, and each R is an independently selected monovalent radical, such as discussed hereinbelow:

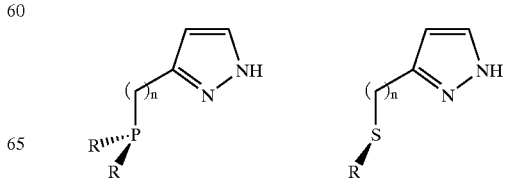

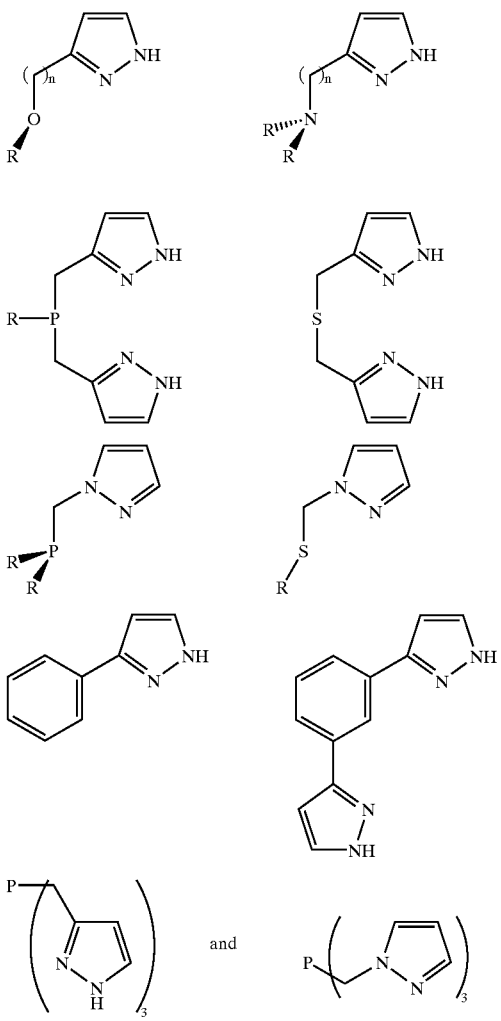

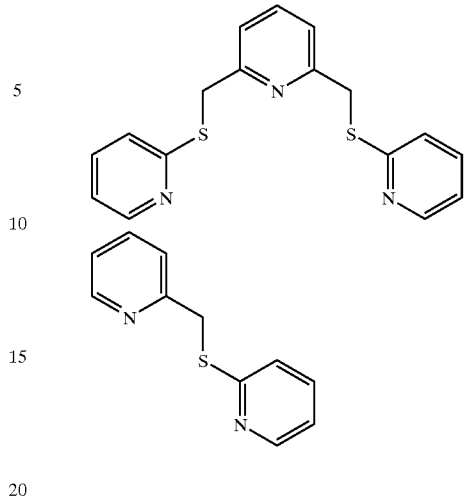

Analogous structures wherein the 2-thiopyridyl group(s) are replaced by 2-thioimidazole groups are also included.

Still further, the present organic ligands may be selected from

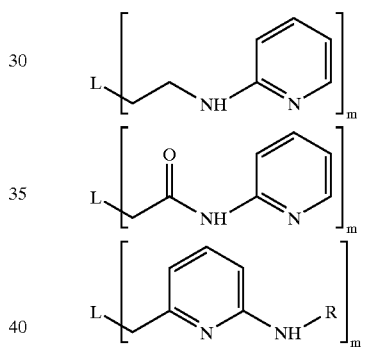

wherein L is selected from S, NH, NR, P, N, SR, PR and PR$_2$, "m" is an integer selected from 1, 2 or 3, and each R is independently selected from monovalent radicals, preferably monovalent substantially hydrocarbyl radicals.

In another embodiment, the organic ligand contains pyridyl groups conjoined by amido linkages, such as according to the following structure:

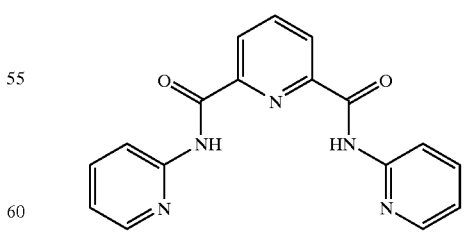

Additionally, organic ligands in accordance with the present invention may be selected from:

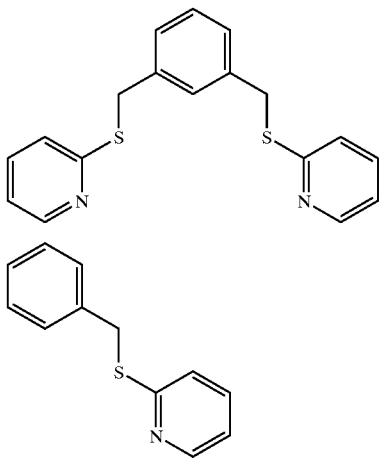

In a preferred aspect of the invention, that is, with respect to hydration of terminal alkynes, a ligand molecule is selected so as to afford a transition metal complex represented by the following formulas:

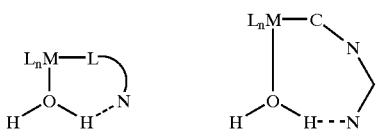

In these formulas, M represents a transition metal atom, $L_n$ represents generic solubilizing ligands of the metal, and L and N together represent a chelating ligand. In the L—N chelating ligand, N is preferably part of a heterocycle and L is a "soft" heteroatom, such as P, S, N, As or Se, separated from N (which can be O) by one atom. As demonstrated herein, the chemical cooperativity generated by such a transition metal complex can afford novel catalytically driven reactivities, such as in the anti-Markovnikov hydration of terminal alkynes.

Utilizing the design principle outlined above, a substituted 2-(diphenylphosphino)imidazole ligand 1 is prepared in 51% yield by lithiation of 4-tert-butyl-1-methylimidazole at C-2, followed by quenching with ClPPh$_2$. Two moles of 1 rapidly displace two acetonitrile ligands from CpRu(CH$_3$CN)$_3$ OTf in the presence of 5 equivalents water to give (after crystallization) a 98% yield of catalyst 2, the structure of which has been determined by X-ray crystallography. The molecule has a piano stool structure having stable hydrogen bond network, wherein the two N—H distances are unequal. However, solution NMR at ambient temperature shows that both phosphines are equivalent, so a rapid conformational change is proposed. This reaction is illustrated in the following scheme:

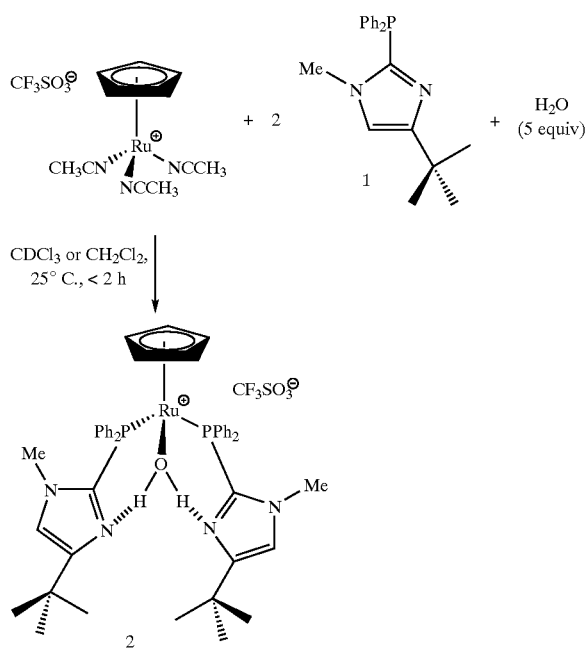

A transition metal moiety of the present invention is partially complexed by at least one of the present organic ligands. The transition metal moiety may be a moiety of a metal selected from Group 1B metals, Group IIB metals, Group IIIB metals, Group IVB metals, Group VB metals, Group VIB metals, Group VIIB metals and Group VIIIB metals. Preferably, the transition metal moiety includes a metal selected from chromium, manganese, iron, cobalt, nickel, copper, zinc, zirconium, niobium, molybdenum, ruthenium, rhodium, palladium, silver, hafnium, tantalum, tungsten, rhenium, osmium, iridium, platinum and gold. For alkyne hydration, the transition metal moiety preferably contains ruthenium.

The present transition metal complexes preferably are soluble in the liquid medium in which such complexes are present or are used. The organic ligands may include one or more substituents, for example, one or more polar substituents and/or non-polar substituents, effective to increase the solubility of the ligand/transition metal complex in a given liquid medium. In addition, the present compositions may include one or more other or additional components, such as silver or thallium salts, acids, bases and the like, in an amount effective to interact with or otherwise affect the complex, for example, to activate the complex and/or to enhance the activity of the complex to facilitate a desired chemical reaction.

The present invention includes within its scope the present ligands and complexes as described herein and any and all substituted counterparts thereof. For example, unless otherwise expressly disclosed to the contrary, one or more of the hydrogen (H) substituents included in the present ligands can be replaced by another monovalent radical, such as a hydrocarbyl radical. Such substituted ligands, as well as the ligands with the hydrogen substituents, are included within the scope of the present invention. In addition, any and all isomers, tautomers, enantiomers, and mixtures thereof of the present ligands are included within the scope of the present invention.

Examples of monovalent radicals that may be included as substituents in the present ligands, for example, as the R groups, include, but not limited to, monovalent hydrocarbon or hydrocarbyl groups, such as alkyl, alkenyl, alkynyl, aryl, alkyl aryl, alkenyl aryl, alkynyl aryl, aryl alkyl, aryl alkenyl, aryl alkynyl and cyclic monovalent hydrocarbon groups; halo such as F, Cl, Br and I; NH$_2$; NO$_2$; alkoxy; alkylthio; aryloxy; arylthio; alkanoyl; alkanoyloxy; aroyl; aroyloxy; acetyl; carbamoyl; alkylamino; dialkylamino; arylamino; alkylarylamino; diarylamino; alkanoylamino; alkylsulfinyl; alkylsulfenyl; alkylsulfonyl; alkylsulfonylamido; azido; benzyl; carboxy; cyano; guanyl; guanidino; imino; phosphinyl; silyl; thioxo; uredido or vinylidene or where one or more carbon atoms are replaced by one or more other species including, but not limited to, N, O, P, or S. The term "substantially hydrocarbyl radical" as used herein refers to a radical in which the number of carbon and hydrogen atoms are at least about 50%, and preferably at least about 70%, or at least about 80%, of the total number of atoms in the radical.

The present invention includes methods for producing a hydrolysis product. Such methods comprise contacting a hydrolysis reactant in the presence of a composition in accordance with the present invention in an amount effective to facilitate the hydrolysis of the hydrolysis reactant to the hydrolysis product. This contacting occurs at effective hydrolysis conditions. Such hydrolysis reaction conditions vary widely depending on many factors, such as the reactants and complex being employed, the concentrations of the reactants and complex, the desired product and other factors. However, such reaction conditions are not of critical importance in the present invention and may be selected from conditions conventionally used in similar reactions. Therefore, a detailed presentation of such conditions is not set forth herein.

The hydrolysis reactant preferably is selected from compounds including amide bonds, nitriles, phosphate esters, and cyanide ions.

Compounds including amide bonds which may be hydrolyzed in accordance with the present invention include, but are not limited to, formamide, acetamide, N-methylacetamide, N,N-dimethylacetamide, N,N-diethylacetamide, propionamide, N-methylpropionamide, N,N-dimeethylpropionamide, N,N-diethylpropionamide, butyramide, N-methylbutyramide, N,N-dimethylbutyramide, acrylamide, N-methylacrylamide, N,N-dimethylacrylamide, benzamide, N-methylbenzamide, N,N-dimethylbenzamide, N,N-diethylbenzamide, o-, m-, and p-toluamides and their N-alkylated derivatives, acetanilide, o-, m-, and p-acetotoluidides, 2-acetamidophenol, 3-acetamidophenol, 4-acetamidophenol, N-acylated amino acids, glycylglycine, alanylalanine, and other polypeptides and proteins.

Nitriles which may be hydrolyzed in accordance with the present invention include, but are not limited to, linear or branched saturated alphatic $C_2$–$C_{18}$ mono- and $C_3$–$C_{19}$ dinitriles and phenyl derivatives thereof, $C_4$–$C_{13}$ saturated alphatic mono- and $C_5$–$C_{14}$ dinitriles, $C_3$–$C_{18}$ linear or branched olefinically unsaturated alphatic nitrites, $C_6$–$C_{13}$ olefinically unsaturated alicyclic nitrites, $C_7$–$C_{14}$ aromatic mono- and dinitriles $C_6$–$C_8$ heterocyclic nitrogen and oxygen mononitriles, $C_3$–$C_4$ cyanoalkanoic amides, $C_2$–$C_{12}$ saturated aliphatic cyanohydrins or hydroxynitriles, and mixtures of the above-described nitrites.

Specific examples include, but are not limited to, acetonitrile, propionitrile, buytronitrile, acrylonitrile, benzonitrile, and substituted derivatives.

Phosphate esters which may be hydrolyzed in accordance with the present invention include, but are not limited to, trialkyl phosphates, triaryl phosphates, dialkyl aryl phosphates, alkyl diaryl phosphates, dialkyl phosphates including DNA and RNA derivatives, diaryl phosphates, alkyl aryl phosphates, alkyl phosphates, aryl phosphates, and analogous phosphonic acid derivatives.

Further, the present invention includes methods for converting carbon dioxide. Such methods comprise contacting carbon dioxide in the presence of a composition in accordance with the present invention in an amount effective to facilitate the conversion of the carbon dioxide to a conversion product. The contacting occurs at effective carbon dioxide conversion conditions. Such reaction conditions vary widely depending on many factors, such as the complex being employed, concentrations of the carbon dioxide and complex, the desired product and other factors. However, such conditions are not critical in the present invention and may be selected from conditions conventionally utilized in similar carbon dioxide conversion reactions. Therefore, a detailed presentation of such conditions is not set forth here.

The carbon dioxide conversion product preferably is selected from ureas, carbamates and carbonates.

Another group of chemical reactions facilitated by the present metal complexes is illustrated by the reaction of alkenes with water to produce the corresponding alcohol.

Without wishing to limit the invention to any particular theory of operation, it is believed that the reaction between water and ethylene can be facilitated using the present metal complexes in accordance with the mechanism given below:

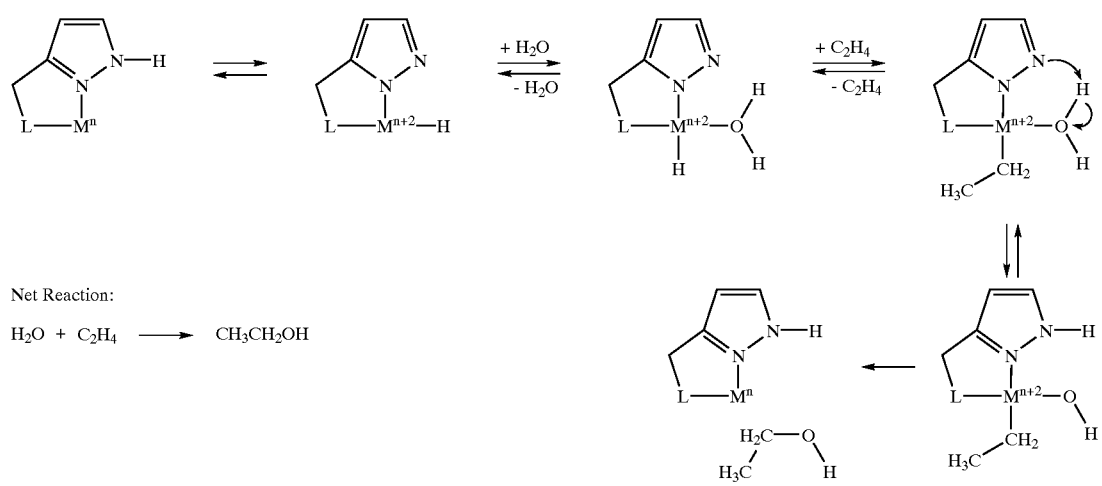

Net Reaction:

$H_2O + C_2H_4 \longrightarrow CH_3CH_2OH$

Similar reaction mechanisms can be envisioned for reactions of other alkenes or alkynes with water, alcohols, ammonia and amines. These reactions are conducted by contacting the reactants together with the complex in accordance with the present invention at effective reaction conditions to obtain the desired product or products. Such reaction conditions can vary widely depending on many factors, such as the reactants and complex being employed, the concentrations of the reactants and complex, the desired product or products and other factors. However, such reaction conditions are not of critical importance in the present invention and may be selected from conditions conventionally used in similar reactions. Therefore, a detailed presentation of such conditions is not set forth here.

Nonetheless, a representative reaction and conditions for the hydration of terminal alkynes is set forth below:

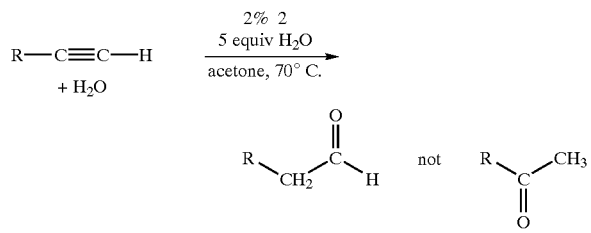

In this reaction, compound 2 is by far the best catalyst to date for the hydration of terminal alkynes to give aldehydes, rather than the isomeric ketones, showing selectivities of up to 1000 to 1.

The following mechanism is proposed to account for the observation of anti-Markovnikov hydration of alkynes:

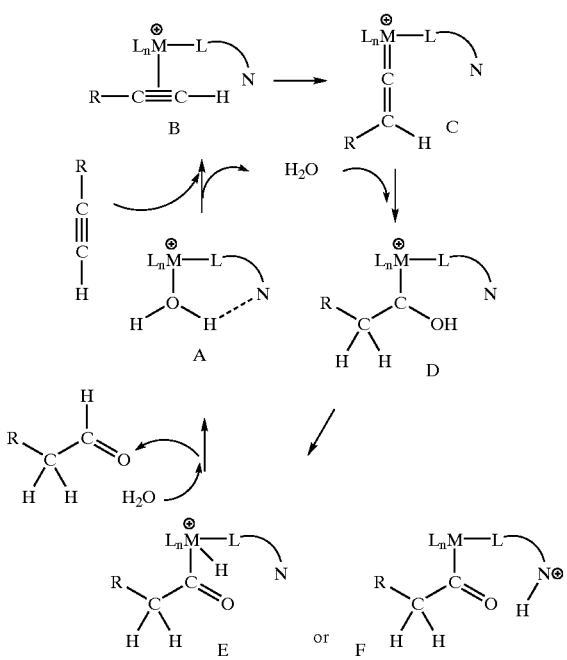

It has been proposed that ketone products are the result of attack of water on alkyne π-complexes such as B. In contrast, for aldehyde formation, likely intermediates include complexes with ligands such as alkyne (B), vinylidene (C), hydroxycarbene (D), or acyl and hydride (E). Reductive elimination from E could lead to aldehyde product. Any of the conversions between A and E could conceivably be aided by the presence of suitably-placed proton or hydrogen-bond donating groups; moreover, aldehyde production could proceed by acyl protonation in an alternative intermediate (F).

The present ligands can be produced from inexpensive and readily available materials, using chemical synthesis techniques well known in the art. To illustrate, many of the present ligands are derived from or based on pyrazole, and can be produced following one of two synthetic routes. In the first route, pyrazole is converted to an electrophilic precursor, whereas in the second route the pyrazole precursor is the nucleophile.

Preparation of Electrophilic Pyrazole Precursor

Pyrazole 1 is converted into chloride 4 in accordance with the following reaction sequences:

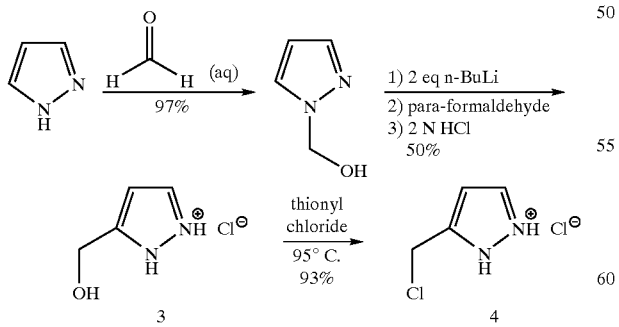

It has been found that an organic solvent is unnecessary in the first step wherein the yield exceeded 95%. The protected pyrazole can then be lithiated with two equivalents of an alkyllithium, such as n-butyllithium, and the pyrazole moiety is than alkylated with formaldehyde. Subsequent deprotection in hydrochloric acid yielded 3. Alcohol 3 is then converted to chloride 4 with thionyl chloride, as noted above.

Use of the Electrophilic Pyrazole Precursor

Pyrazole ligands can be prepared in accordance with the following general reaction:

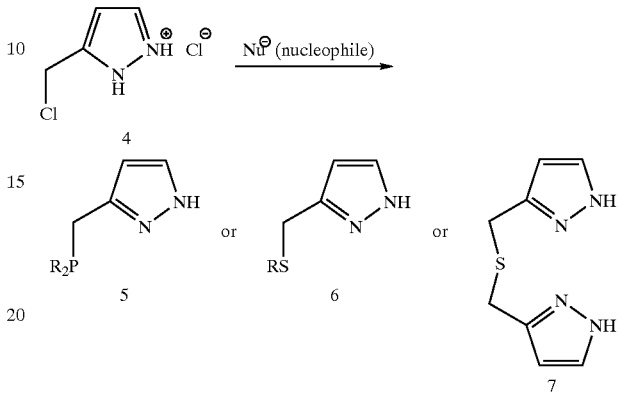

The desired ligand 5 can be obtained using three equivalents of lithium diphenylphosphide. Lithium thiomethoxide and sodium disulfide also can be used, giving ligands 6 and 7, respectively. Further, this synthetic route gives access to mono-pyrazole ligands with the general structure of 5 and 6 and (bis-pyrazole)-ligands, such as 7. By changing the R substituent and the tethered ligating atom, a library of ligands with varying steric hindrances and electronic environments can be produced. In addition, solubility properties of the resulting metal complexes can be drastically altered with the use of thiols, such as commercially available 2-mercaptoethane-sulfonic acid sodium salt or 2-mercaptoethanol.

Direct Alkylation of Nucleophilic Pyrazole Precursors

The pyrazole moiety as a carbon nucleophile can be used on electrophiles to obtain pyrazole-based ligands in a one-pot synthesis. Examples of such ligands include compounds 9–11.

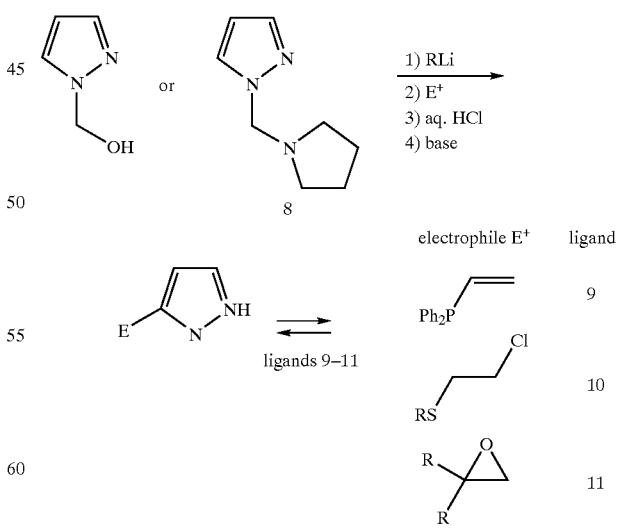

Preparation of Isoelectronic and Isosteric Pyrazole Ligands Incapable of Hydrogen Bonding and Proton Transfer Isoelectronic and isosteric ligands can be prepared according to a synthetic route illustrated below:

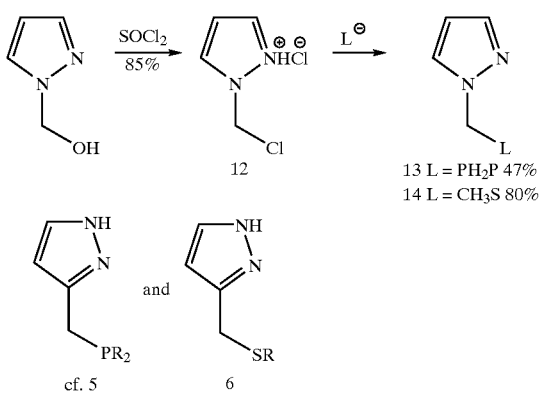

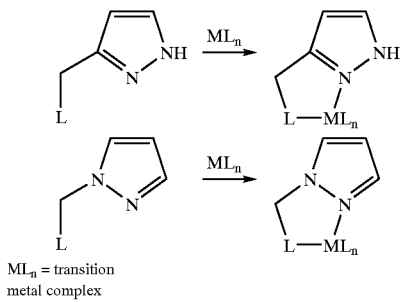

ML$_n$ = transition metal complex

In one embodiment, the metal has an oxidation state that is unlikely to oxidatively add to the nitrogen-hydrogen bond of a pyrazole moiety. In addition, the formation of stereoisomeric products preferably is reduced. The metals selected preferably are those likely to give four-coordinate complexes, an example of which is Pd(II), as shown by the following complexation reactions:

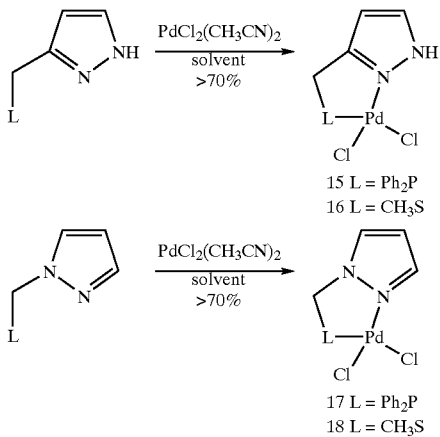

In another embodiment, the metal's oxidation state and structural criteria described above is retained and, in addition, the metals are selected based on a change in the relative pK$_a$s of their respective aquo-metal ions. Examples include metals such as platinum(II), zinc(II), and nickel(II), which have aquo-metal ions with pK$_a$s of 4, 9 and 10, respectively, whereas the aquo-metal ion of palladium(II) has a pKa of 2.

Metals capable of making hexa- or penta-coordinated complexes may be employed. Examples include chromium, manganese, iron, cobalt, copper, zinc, molybdenum, ruthenium, rhenium, palladium, silver, hafnium, tantalum, tungsten, rhodium, osmium, iridium, platinum and gold. Still more preferably, the transition metal moiety is a moiety of a metal selected from iron, cobalt, copper, zinc, palladium and ruthenium.

The complexes can be substituted with various ligands such as triflate, acetate, water or alcohol. The ligand selections allow adjusting the solubilities of the complexes to enable the hydrolysis of amides, phosphodiesters and nitriles and the addition to carbon dioxide to be conducted in polar or nonpolar solvents.

The present complexes are effective as hydrolysis reagents or reaction facilitators, such as catalysts. For example, it has been found that the complex 19, set forth below, is catalytic toward the hydrolysis of N,N-dimethylacetamide and gives a more than 9% yield of the hydrolysis products:

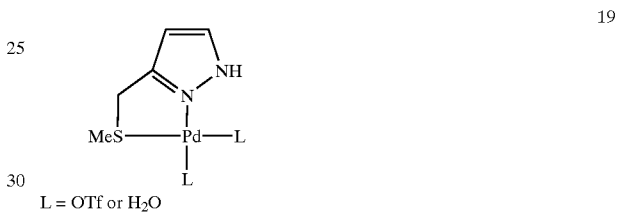

L = OTf or H$_2$O

However, when complex 17 noted previously is used with dimethylformamide in acetonitrile and water at 75° C., amide cleavage products in 4% yield are provided, while complex 19 is found to be inactive. Although these reactions are slow and only two catalytic turnovers were achieved, these results are preliminary in nature. The conditions for the hydrolysis can be adjusted to provide enhanced results.

Hydration of Terminal Alkynes

The hydration of alkynes historically requires catalysis by strong acids and environmentally objectionable Hg(II), or transition metal salts (RuCl$_3$, RhCl$_3$, PtX$_2$, NaAuCl$_4$), and all of is these conditions give Markovnikov addition of water to the terminal alkyne, with formation of the methyl ketone. Anti-Markovnidov hydration can be achieved indirectly by addition of a stoichiometric amount of a borane or silane B—H or Si—H bond, followed by oxidation. Thus far, the only report of catalytic anti-Markovnikov hydration of terminal alkynes is the work of Tokunaga and Wakatsuki, who reported the combined use of (C$_6$H$_6$)RuCl$_2$(C$_6$F$_5$PPh$_2$) (10 mol %) and C$_6$F$_5$PPh$_2$ (30 mol %) typically gave aldehydes in 50–75% yield, with aldehyde-to-ketone selectivities of about 10 to 1. Hindered alkynes such as phenyl- or tert-butylacetylene gave less than 2% yields of product.

In contrast, we report that (compound 2) works even for tert-butylacetylene at the 2% level, giving yields in excess of 90%. Reactions of 2 with terminal alkynes were examined under the same conditions in order to assess the scope and limitations of the method. Alkyl-substituted alkynes work the best. A tert-butyl group slows hydration but on heating at about 90° C., aldehyde is formed in 91% yield. In contrast, the Tokunaga-Wakatsuki system gave 0.9% yield of aldehyde. Phenylacetylene reacts about as sluggishly as tert-butylacetylene, but in this case NMR spectroscopy confirms that 2 mol % 2 disappears after 21 h and hydration stops unless additional catalyst is added. (See Table 1 hereinafter)

Remarkably, alkynes with propargylic oxygen substituents are tolerated. Substrates with acid-sensitive protecting groups such as t-BuMe$_2$Si and tetrahydropyranyl are hydrated to give aldehydes made previously in multistep syntheses.

It is anticipated that, analogously to the addition of water to terminal alkynes, primary alcohols and amines can be catalytically added to the site of unsaturation following the cooperative scheme described hereinabove.

In conclusion, clear evidence is provided that the cooperative effects of a Ru(II) center and two imidazole groups on phosphine ligands create a superior single-component catalyst for the anti-Markovnikov hydration of terminal alkynes under near-neutral reaction conditions. Improvements in catalyst design, the mode of catalyst deactivation, and the extension of this design principle to other structures and reactions are all topics of active investigation in these laboratories.

Preferred ligands for use in the aforementioned addition reactions include those mentioned previously above. Also preferred are ligands containing one or more imidazole groups as the sole heterocycle(s) in the molecule, or in conjunction with one or more pyridyl groups. A partial compilation of these preferred ligands is illustrated hereinbelow:

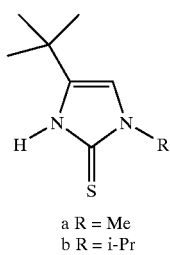

1 a R = Me
b R = i-Pr

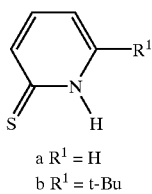

2 a R$^1$ = H
b R$^1$ = t-Bu

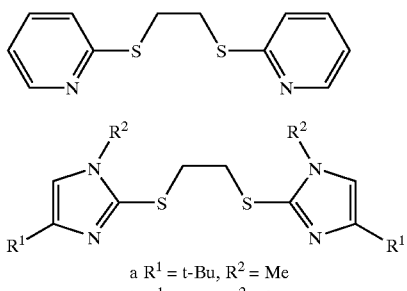

3

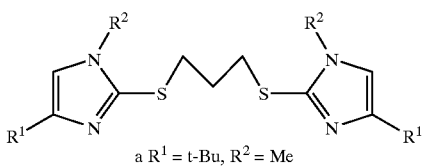

4 a R$^1$ = t-Bu, R$^2$ = Me
b R$^1$ = t-Bu, R$^2$ = i-Pr

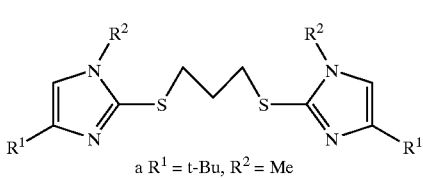

5 a R$^1$ = t-Bu, R$^2$ = Me

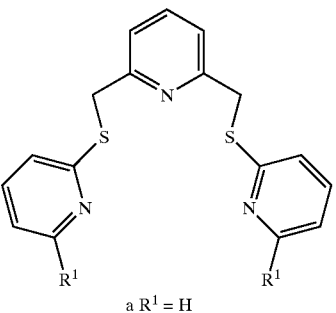

6 a R$^1$ = H
b R$^1$ = t-Bu

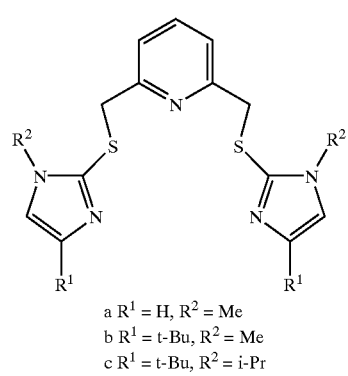

7 a R$^1$ = H, R$^2$ = Me
b R$^1$ = t-Bu, R$^2$ = Me
c R$^1$ = t-Bu, R$^2$ = i-Pr

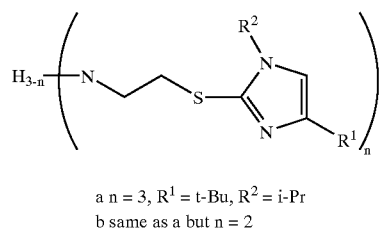

8 a n = 3, R$^1$ = t-Bu, R$^2$ = i-Pr
b same as a but n = 2

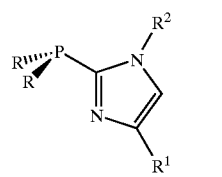

9 a R$^1$ = t-Bu, R$^2$ = Me, R = Ph
b R$^1$ = t-Bu, R$^2$ = i-Pr, R = Ph
c R$^1$ = t-Bu, R$^2$ = i-Pr, R = t-Bu
d R$^1$ = t-Bu, R$^2$ = Me, R = Me

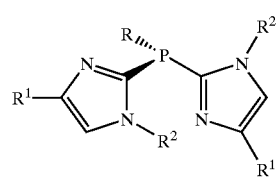

10 a R$^1$ = t-Bu, R$^2$ = Me, R = Ph
b R$^1$ = t-Bu, R$^2$ = Me, R = Me

-continued

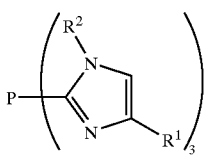

a R¹ = t-Bu, R² = i-Pr    11

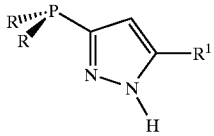

a R¹ = t-Bu, R² = Ph    12

The following non-limiting examples illustrate certain aspects of the present invention.

EXAMPLE 1

Preparation of 3-(diphenylphosphinomethyl) pyrazole Having the Following Structure

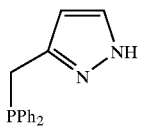

To a solution of tetrahydrofuran (100 ml) and triphenylphosphine (3.56 g, 13.6 mmol) at room temperature is added lithium (0.100 g, 14.5 mmol). The reaction mixture is stirred at room temperature for 2 hours at which time the lithium has dissolved. The bright red solution is cooled to 0° C., and 3-(chloromethyl)pyrazole hydrochloride (0.960 g, 6.8 mmol) is added at once. The ice bath is removed and the reaction solution is allowed to stir an additional 2 hours. Degassed ethanol (40 ml) is added to the reaction mixture followed by diethyl ether (100 ml). The organic phase is separated and the aqueous phase extracted with diethyl ether (2×25 ml). The organic phases are combined and dried over magnesium sulfate, filtered and concentrated. The crude residue is purified by chromatography (SiO₂, 50% ethyl acetate/petroleum ether) to give purified 3-(diphenylphosphinomethyl)pyrazole as a cloudy white oil in 77% yield (2.81 g, 10.6 mmol). This material is characterized as follows: $^1$H NMR (CDCl₃, 500 MHz) δ7.43 (m,4H), 7.41 (d, J=2.0 Hz, 1H), 7.34 (m, 6H), 5.99 (d, J=2.0 Hz, 1H), 3.47 (s, 2H); $^{13}$C{$^1$H} NMR (CDCl₃, 125 MHz) δ138.16 (d, 14.3 Hz), 132.97 (d, J=18.6 Hz), 129.11, 128.73 (d, J=6.6 Hz), 105.18 (d, J=5.1 Hz), 27.14 (d, J=6.2 Hz) MS m/z 265.9, 182.9 (M—C₄H₃N₂).

EXAMPLE 2

Preparation of cis-Dichloro-[(η²-P,N)-3-(Diphenylophosphinomethyl)pyrazole]palladium(II) Having the Following Structure

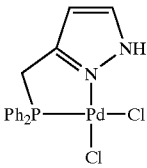

To 3-(diphenylphosphinomethyl)pyrazole (0.124 g, 0.46 mmol) and bis(acetononitrile)palladium(II) dichloride (0.121 g, 0.46 mmol) is added degassed methanol (10 ml). The reaction slurry is stirred 14 hours at room temperature. The reaction slurry is filtered and the solid is washed with petroleum ether (2×10 ml). The solid residue is placed under vacuum to give pure cis-dichloro-(η²-P,N)-3-[(diphenylphosphino-methyl)pyrazole]palladium(II) as a yellow solid in 93% yield (0.192 g, 0.43 mmol). Crystals for X-ray analysis are grown with the slow evaporation of methanol from a solution. This material is characterized as follows: $^1$H NMR (DMSO-d₆, 200 MHz) δ12.90 (s, 1H), 7.88 (m, 5H), 7.60 (m, 6H), 6.54 (bs, 1H), 4.03 (d, J=13 Hz, 2H); $^{13}$C{$^1$H} NMR (DMSO-d₆, 50 MHz) δ152.38 (d, J=6.5 Hz), 134.09, 133.09 (d, J=11.0 Hz), 132.28 (d, J=3.1 Hz), 129.14 (d, J=11.8 Hz), 127.67 (d, J=55.4 Hz), 104.56 (d, J=12.9 Hz), 28.68(d, J=31.9 Hz); $^{31}$P{$^1$H} NMR (DMSO-d₆, 80 MHz) δ46.67; M/S FAB 439, 440, 441, 442, 443, 444, 445, 446, 447.

EXAMPLE 3

Preparation of 1-(Diphenylphosphinomethyl) pyrazole Having the Following Structure

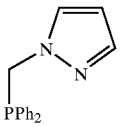

Diphenylphosphine (2.642 g, 14.2 mmol) is placed into a Schlenk flask with degassed tetrahydrofuran (50 ml). The solution is cooled to −78° C. and n-butyllithium (8.4 ml, 1.6 M in hexanes, 15.0 mmol) is added dropwise. The red solution is stirred at −78° C. for an additional 1 hour then the cooling bath is removed and the solution is stirred for 3 hours. The red solution is cooled to 0° C. and 1-(chloromethyl)pyrazole hydrochloride (0.698 g, 4.56 mmol) is added at once. The ice bath is removed and the reaction is stirred for 11 hours before adding degassed methanol (25 ml) and water (20 ml). The organic phase is separated and the aqueous phase is extracted with diethyl ether (3×10 ml). The organic phase is dried over magnesium sulfate, filtered and concentrated. The crude material is purified by chromatography (SiO₂, 10% ethyl acetate/petroleum ether) to give 1-(diphenylphosphinomethyl) pyrazole as a white solid in 47% yield (0.574 g, 2.16 mmol). This material is characterized as follows: $^1$H NMR (CDCl₃, 500 MHz) δ7.49 (dd, J=2.0, 0.5 Hz, 1H), 7.45–7.40 (m, 4H), 7.40–7.35 (m, 6H), 7.25 (dd, J=2.5, 0.5 Hz, 1H), 6.19 (dd, J=2.5, 2.0 Hz, 1H), 4.91 (d, J=4.5 Hz, 2H); $^{13}$C{$^1$H} NMR (CDCl₃, 125 MHz) δ139.50, 136.04 (d, J=13.4 Hz), 133.18

(d, J=19.3 Hz), 129.34, 129.49, 128.95 (d, J=6.4 Hz), 106.11, 53.01 (d, J=16.0 Hz); $^{13}P\{^1H\}$ NMR (CDCl$_3$, 80 MHz) δ−14.98.

EXAMPLE 4

Preparation of cis-Dichloro-[(η$^2$-P,N)-1-(Diphenylphosphinomethyl)pyrazole]palladium(II) Having the Following Structure

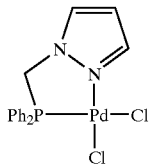

A flask is charged with 1-(diphenylphosphino-methyl)pyrazole (0.049 g, 0.184 mmol) and bis(acetonitrile)palladium(II) dichloride (0.048 g, 0.186 mmol). Degassed methanol (5 ml) is added. The resulting yellow solution instantaneously becomes cloudy. The slurry is stirred for 5 hours at room temperature then filtered through a glass frit. The precipitate is washed with dichloromethane then dried under vacuum (0.05 mmHg) giving cis-dichloro-[(η$^2$-P,N)-1-(diphenylphosphinomethyl)pyrazole]palladium(II) (0.068 g, 0.153 mmol) in 83% yield. This material is characterized as follows: $^1$H NMR (DMSO-d$_6$, 200 MHz) δ8.24 (m, 1H), 8.09 (m, 1H), 8.00–7.80 (m, 4H), 7.75–7.40 (m, 6H), 6.61 (m, 1H), 5.47 (d, 8.2 Hz).

EXAMPLE 5

Preparation of 3-(Methylthiomethyl)pyrazole Having the Following Structure

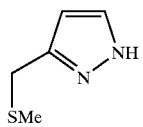

3-(Chloromethyl)pyrazole hydrochloride (1.77 g, 11.6 mmol) is dissolved in dried tetrahydrofuran (100 ml) under nitrogen atmosphere. At room temperature, MeSLi (1.25 g, 2.32 mmol) is added to the mixture. The solution becomes slightly pink. The reaction is stirred for 10 hours and quenched with water (3 ml). Then the solvent is distilled off by rotary evaporation. The organic phase is extracted with ethyl acetate (3×10 ml). The organic phases are combined, dried over magnesium sulfate, filtered and concentrated. The crude residue is purified by Kugelrohr distillation at 140° C./0.5 mmHg to give 3-(methylthiomethyl)pyrazole as a clear oil in 82% yield (1.22 g, 9.52 mmol). This material is characterized as follows: $^1$H (CDCl$_3$, 500 MHz) δ9.2 (broad, 1H), 7.55 (d, J=2.0 Hz, 1H), 6.24 (d, J=2.0 Hz, 1H), 3.77 (s, 2H), 2.06 (s, 3H) ppm. $^{13}$C (CDCl$_3$, 500 MHz) δ146.31 (broad), 132.85, 104.78, 30.08, 15.42 ppm. FT-IR (NaCl, cm$^{-1}$) 3519, 2886, 1467, 1340, 1105.

EXAMPLE 6

Preparation of Cis-Dichloro-[(η$^2$-S,N)-(3-methylthiomethyl)pyrazole]palladium(II) Having the Following Structure

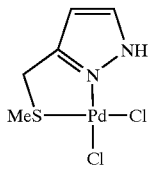

To a solution of 3-(methylthiomethyl)pyrazole (0.67 g, 5.25 mmol) in methanol (10 ml) under nitrogen atmosphere at room temperature is added PdCl$_2$ (1.36 g, 5.25 mmol). The Pd complex dissolves in about 5 minutes with stirring. The reaction is stirred for 12 hours, during which time orange solid forms. The reaction mixture is filtered, and the solid is washed with methanol (2×5 ml). The solid residue is placed under vacuum to give pure cis-dichloro-[(η$^2$-S,N)-(3-methylthiomethyl)pyrazole]palladium(II) in 80% yield (1.36 g, 4.46 mmol). This material is characterized as follows: $^1$H (DMSO-d$_6$, 500 MHz) δ12.5 (s, 1H), 7.89 (d, J=2.0 Hz, 1H), 6.54 (d, J=2.0 Hz, 1H), 4.31 (d, J=16.5 Hz, 1H), 3.99 (d, J=16.5 Hz, 1H), 2.62 (s, 3H) ppm. $^{13}$C (DMSO-d$_6$ 500 MHz) δ154.92, 133.44, 104.61, 35.06, 23.15 ppm. FT-IR (KBr, cm$^{-1}$) 3493, 3309, 2921, 1516, 1422, 1375.

EXAMPLE 7

Preparation of the Compound Having the Following Structure

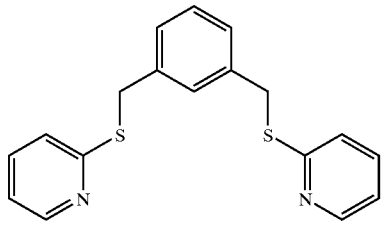

To a stirred suspension of NaH (65.4 mg of 80% suspension in mineral oil, 2.18 mmol) in dry N,N-dimethylformamide (2 ml) in an ice-cooled Schlenk flask is added 2-mercaptopyridine in two portions (221.0 mg, 1.99 mmol). Bubbling is noted. After 1 minute the ice bath is removed. After another 2 minutes the ice bath is returned, and after 4 minutes solid α,α'-dibromo-m-xylene (256.5 mg, 0.972 mmol) is added in one portion, dissolving within 0.5 minutes. Within 2 minutes the mixture becomes too thick to stir, and the ice bath is removed. After 2.5 hours a solution of water and sat. aq. NaHCO$_3$ (10 ml each) is added to the mixture. The resulting cloudy mixture is extracted with CH$_2$Cl$_2$ (3×10 ml) and ethyl acetate (3×10 ml). The combined organic extracts are washed with water (1×10 ml), brine (1×10 ml), and dried over MgSO$_4$ and filtered. The aqueous washes were back-extracted with ethyl acetate (1×10 ml). The combined filtrates are concentrated by rotary evaporation leaving slightly cloudy yellowish oil (574.9 mg) which is purified by radial chromatography using a 4 mm thick SiO$_2$ plate and ethyl acetate-petroleum ether mixtures. Product-containing fractions are concentrated by rotary evaporation, the residue is swirled with petroleum ether and concentrated. After storage on the high-vacuum line, product remains as colorless oil (302.5 mg, 96% yield). This material is characterized as follows: $^1$H NMR (CDCl$_3$, 500 MHz) δ8.45 (ddd, J=1.0, 2.0, 5.0 Hz, 2H, pyridine H-6), 7.46 (ddd, J=1.9, 7.4, 8.1 Hz, 2H, pyridine H-4), 7.46 (s, 1H), 7.29 (dd, J=1.6, 7 Hz, 2H), 7.22 (dd, J=6.7, 8.4 Hz, 1H), 7.15 (td, J=1.0, 8.1 Hz, 2H, pyridine H-3), 6.98 (ddd, J=1.1, 5.0, 7.4 Hz, 2H), 4.42 (s, 4H) ppm. $^{13}$C{$^1$H} NMR (CDCl$_3$, 125 MHz) δ158.72, 149.35, 138.15, 135.89, 129.57, 128.59, 127.69, 122.04, 119.53, 34.27 ppm. Analysis calculated for: C$_{18}$M$_{16}$N$_2$S$_2$; C, 66.63; M, 4.97; N, 8.63. Found: C, 66.67; H, 4.88; N, 8.58.

EXAMPLE 8

Preparation of the Palladium(II) Complex of the Product of Example 7

The product of Example 7 is stirred with palladium(II) acetate or trifluoroacetate in a solvent such as dichloromethane, chloroform, methanol, or toluene at a temperature and for a time needed to produce the desired palladium(II) complex. Alternatively, tetrakis(acetonitrile) palladium(II) trifluoromethanesulfonate is used.

The desired complex can also be made in accordance with the following reaction scheme.

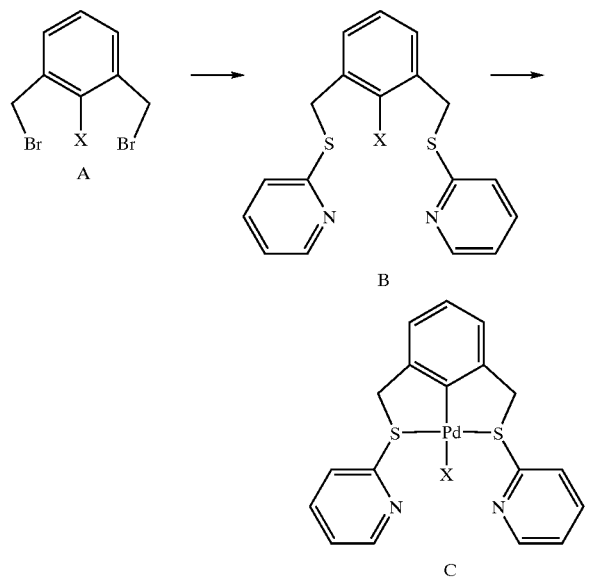

A solution of α,α'-2-tribromo-m-xylene (compound A, X=Br) in an appropriate organic solvent such as N,N-dimethylformamide or acetonitrile or mixture of solvents is treated with a solution made from 2-mercaptopyridine and a suitable base, such as sodium hydride or potassium t-butoxide, in an appropriate organic solvent or mixture of solvents. After an appropriate time at an appropriate temperature (e.g. 1 h at 25° C.), the mixture is worked up to isolate product B. Other 2-functionalized α,α'-dibromo-m-xylenes can also be used.

The product B mixed with an appropriate palladium complex such as tetrakis(triphenylphosphine)palladium(0), tris(benzylideneacetone)dipalladium(0), palladium(II) acetate or trifluoroacetate, bis(acetonitrile)palladium(II) trifluoromethanesulfonate with or without other additives such as phosphines, amines, inorganic bases or acetonitrile in an appropriate solvent such as acetonitrile, dichloromethane, chloroform, methanol, or toluene at a temperature and for a time needed to produce the desired palladium(II) complex C.

EXAMPLE 9

Preparation of 2,6-Pyridine dicarboxamide, N,N$^1$-bis(2-pyridinyl) Having the Following Structure

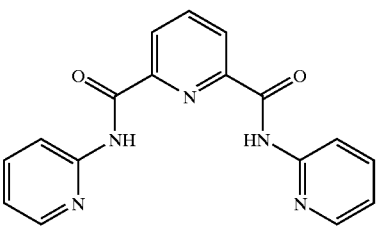

A solution of 2,6-pyridine dicarbonyl dichloride (4.34 g, 21.2 mmol) and 4-dimethylamino-pyridine (0.259 g, 2.12 mmol) in methylene chloride (10 ml) is prepared under nitrogen. In a separate flask, a solution of 2-aminopyridine (4.00 g, 42.4 mmol) and triethylamine (5.77 ml, 42.4 mmol) in methylene chloride (10 ml) is prepared. The aminopyridine solution is added over 10 minutes to the pyridine dicarbonyl dichloride while stirring and refluxing. This causes the solution to change from colorless to light green with a white precipitate. After refluxing the reaction for 3 hours, the mixture is cooled and the precipitate filtered, and washed with cold methanol (3×5 ml). The brown filtrate is then washed with water (3×10 ml). After washing the aqueous extract once with methylene chloride (5 ml), the combined organic layer is stripped of solvent and the resulting solid is recrystallized from pyridine as white needles (4.81 g, 71% yield). This material is characterized as follows:

$^1$H NMR (CDCl$_3$, 200 MHz) δ11.08 (s, 2H), 8.53 (d, J=8 Hz, 2H), 8.40 (d, J=3.8 Hz, 2H), 8.17 (t, J=7.5 Hz, 1H), 7.82 (t, J=7 Hz, 2H), 7.13 (t, J=6.9 Hz, 2H); $^{13}$C (CDCl$_3$, 50 MHz) δ160.46, 149.90, 147.20, 146.28, 137.97, 137.24, 124.26, 118.57, 113.04.

EXAMPLE 10

Preparation of Palladium(II) Complex of Product of Example 9

The product of Example 9 is stirred with a palladium(II) complex such as palladium(II) acetate, or trifluoroacetate, or bis(acetonitrile)palladium(II) dichloride, or tetrakis (acetonitrile)palladium(II) trifluoromethanesulfonate in a solvent such as dichloromethane, chloroform, methanol, or toluene at a temperature and for a time needed to produce the desired palladium(II) complex.

EXAMPLE 11

Preparation of 2,6-pyridine dicarboxamide, N,N[1]-bis(2-methyl-6-pyridinyl) Having the Following Structure

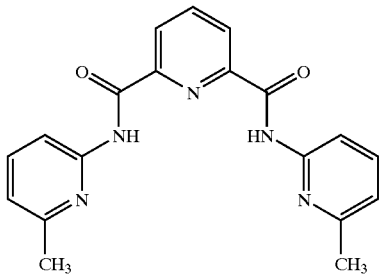

A solution of 2,6-pyridine dicarbonyl dichloride (4.34 g, 21.2 mmol) and 4-dimethylamino-pyridine (0.259 g, 2.12 mmol) in methylene chloride (10 ml) is prepared under nitrogen. In a separate flask, a solution of 2-amino-6-picoline (4.58 g, 42.4 mmol) and triethylamine (5.77 ml, 42.4 mmol) in methylene chloride (10 ml) is prepared. The aminopicoline solution is added over 10 minutes to the pyridine dicarbonyl dichloride while stirring and refluxing. After refluxing the reaction for 3 hours, the precipitate is filtered, and washed with cold methanol (3×5 ml). The brown filtrate is then washed with water (3×10 ml). After washing the aqueous extract once with methylene chloride (5 ml), the combined organic layer is stripped of solvent and the resulting solid is recrystallized from pyridine as white needles (6.47 g, 88% yield). This material is characterized as follows:

$^1$H NMR (CDCl$_3$, 200 MHz) δ11.15 (s, 2H), 8.50 (d, J=7.6 Hz, 2H), 8.33 (d, J=8.2 Hz, 2H), 8.14 (t, J=7.7 Hz, 1H), 7.70 (t, J=7.9 Hz, 2H), 6.98 (d, J=7.4, 2H), 2.56 (s, 6H); $^{13}$C (CDCl$_3$, 50 MHz) δ159.78, 147.56, 137.82, 133.12, 128.08, 123.82, 118.92, 19.27.

EXAMPLE 12

Preparation of palladium(II) Complex of Product of Example 11

The product of Example 11 is stirred with a palladium(II) complex such as palladium(II) acetate or trifluoroacetate, or bis(acetonitrile)palladium(II) dichloride, or tetrakis(acetonitrile)palladium(II) trifluoromethanesulfonate in a solvent such as dichloromethane, chloroform, methanol, or toluene at a temperature and for a time needed to produce the desired palladium(II) complex.

EXAMPLE 13

Hydrolysis of N,N-dimethylacetamide Using cis-dichloro-[η$^2$-S,N-(3-methylthiomethyl)pyrazole]palladium(II) (Product of Example 6)

Cis-dichloro-[η$^2$-S,N)-(3-methylthiomethyl)pyrazole]palladium(II) (0.30 g, 1.0 mmol) is dissolved in N,N-dimethylacetamide (1.74 g, 20 mmol) at room temperature. Silver triflate (0.52 g, 2.0 mmol) is added to the solution. A cloudy precipitate forms, and the reaction mixture is centrifuged. The yellow solution is transferred by pipet into a small vial and diluted with D$_2$O (1.2 g, 60.0 mmol). The reaction mixture is stirred for 2 hours. The first aliquot is taken for analysis by NMR spectroscopy. No peaks of hydrolysis products are observed. The pH is also observed to be around 3.6–4.0. Then the reaction mixture is heated to 75° C. After 1 day at 75° C., 8.7% of hydrolysis products are observed in an analysis of a second aliquot by NMR spectroscopy. After 5 days of heating at 75° C., 8.6% of hydrolysis products are observed by NMR spectroscopy. The pH is also observed to be around 3.6–4.0. The reaction mixture is heated to 90° C., and 9.4% of hydrolysis products are observed. Then triflic acid is slowly added into the mixture reaction until the pH is at 1–2. The mixture reaction is heated to 75° C. 2.5 hours after adding the acid, 21.5% of hydrolysis is observed. The mixture is heated further at 75° C., but no further hydrolysis is observed.

Control Experiments. At pH 3.5–4.0: N,N-Dimethylacetamide (11.9 mg, 1.37 mmol) is mixed with D$_2$O (624 mg, 31.2 mmol). Then trifluoromethanesulfonic acid is added into the reaction mixture until pH is measured as 3.5–4.0. The reaction mixture is heated to 75° C. After 2 and 4 days, no hydrolysis products are observed by NMR spectroscopic analysis of the mixture. At neutral pH: N,N-Dimethylacetamide (4.87 mg, 0.56 mmol) is mixed with D$_2$O (600 mg, 30.0 mmol). The reaction mixture is heated to 85° C. After 8 days, no hydrolysis is observed. Then the reaction mixture is heated to 90° C., and after 21 days, no hydrolysis is observed.

EXAMPLE 14

Hydrolysis of Phosphate Ester Using cis-dichloro-[η$^2$-S,N)-(3-methylthiomethyl)pyrazole]palladium (II) (Product of Example 6)

The product of Example 6, with or without other additives including silver or thallium salts, acids, or bases, is combined with a phosphate ester, such as DNA or RNA, in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the phosphate ester to the desired degree.

EXAMPLE 15

Hydrolysis of Nitrile Component Using cis-dichloro-[(η$^2$-S,N)-(3-methylthiomethyl)]pyrazole palladium(II) (Product of Example 6)

The product of Example 6, with or without other additives including silver or thallium salts, acids, or bases, is combined with a nitrile component, such as acetonitrile, in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the nitrile component to the desired degree.

EXAMPLE 16

Hydrolysis of Cyanide Ion-containing Component Using cis-dichloro-[(η$^2$-S,N)-(3-methylthiomethyl)pyrazole]palladium (II) (Product of Example 6)

The product of Example 6, with or without other additives including silver or thallium salts, acids, or bases, is combined with a cyanide ion-containing component in an appropriate solvent, such as a mixture of water and an organic co-solvent or an organic solvent or mixture of organic solvents. The resulting mixture is allowed to react at an appropriate temperature, such as about 0° C. to about 100° C., for a sufficient time, such as about 1 hour to about 96 hours, thereby providing hydrolysis of the cyanide ion-containing component to the desired degree.

EXAMPLE 17

Conversion of Carbon Dioxide Using cis-dichloro-[($\eta^2$-S,N)-(3-methylthiomethyl)pyrazole]palladium (II) (Product of Ex. 6)

The product of Example 6, with or without other additives including silver or thallium salts, acids, or bases, is combined with other reactants, such as alcohols (e.g., methanol) or amines (e.g., dimethylamine) in an appropriate solvent, such as a mixture of water and an organic co-solvent or an organic solvent or mixture of organic solvents. Carbon dioxide is introduced into the mixture and using the appropriate temperature, such as about 0° C. to about 100° C., and sufficient time, such as about 1 hour to about 96 hours, the desired conversion of carbon dioxide is obtained.

EXAMPLE 18

Alcoholysis of an Amide Using cis-dichloro-q-S,N-(3-methylthiomethyl)pyrazole palladium(II) (Product of Ex. 6)

The product of Example 6, with or without other additives including silver or thallium salts, acids, or bases, is combined with an amide, such as dimethylacetamide, and an alcohol, such as methanol, with or without the use of an appropriate so-solvent, such as excess alcohol or other organic solvent or mixture of organic solvents. The resulting mixture is allowed to react at an appropriate temperature, such as about 0° C. to about 100° C., for a sufficient time, such as 1 hour to about 96 hours, thereby providing alcoholysis of the amide to the desired degree.

EXAMPLE 19

Aminolysis of an Amide Using cis-dichloro-$\eta^2$-S, N-(3-methylthiomethyl)pyrazole palladium(II) (Product of Ex. 6)

The product of Example 6, with or without other additives including silver or thallium salts, acids, or bases, is combined with an amide, such as acetamide, and an amine, such as dimethylamine, with or without the use of an appropriate co-solvent, such as excess amine or other organic solvent or mixture of organic solvents. The resulting mixture is allowed to react at an appropriate temperature, such as about 0° C. to about 100° C., for a sufficient time, such as 1 hour to about 96 hours, thereby providing aminolysis of the amide to the desired degree.

EXAMPLES 20 TO 26

Examples 13 to 19 are repeated except that the product of Example 2 is used in place of the product of Example 6.

EXAMPLES 27 TO 33

Examples 13 to 19 are repeated except that the product of Example 4 is used in place of the product of Example 6.

EXAMPLES 34 TO 40

Examples 13 to 19 are repeated except that the product of Example 8 is used in place of the product of Example 6.

EXAMPLES 41 TO 47

Examples 13 to 19 are repeated except that the product of Example 10 is used in place of the product of Example 6.

EXAMPLES 48 TO 54

Examples 13 to 19 are repeated except that the product of Example 12 is used in place of the product of Example 6.

EXAMPLES 55 TO 64

Hydration of Alkynes

Example 55. Synthesis of P-linked imidazole ligand (compound 1)

In a Schlenk flask equipped with a magnetic stir bar and a rubber septum and cooled in a dry ice-acetone bath, to a solution of 1-methyl-4-tert-butylimidazole (1.50 g, 10.8 mmol) in dry THF (30 mL) was added n-BuLi in hexanes (4.5 mL of 2.4 M solution, 12.0 mmol) over the course of 7 min. The bath temperature was allowed to rise from −78 to −58° C. over the course of 1 h as the solid carbon dioxide disappeared. Using a syringe, ClPPh$_2$ (2.38 g, 10.8 mmol) was added dropwise over about a minute. After 1 h, the cooling bath was removed, and 2 h later the mixture was diluted with water (75 mL). The organic phase was separated and the aqueous phase extracted with CH$_2$Cl$_2$ (3×25 mL). Combined organic phases were washed with water (50 mL) and dried over MgSO$_4$. After filtration, the filtrate was concentrated on a rotary evaporator, leaving 3.96 g of cloudy oil. Purification by radial chromatography under nitrogen gas using petroleum ether followed by EtOAc-petroleum ether mixtures (up to 1 to 10 ratio) allowed separation of less-polar BuPPh$_2$ from more-polar product. The desired product (compound 1) was isolated as a thick oil which crystallized on standing (1.78 g, 5.52 mmol, 51%).

Example 56. Preparation of P-linked Ru (II) complex (compound 2)

In the glovebox, CH$_2$Cl$_2$ (3 mL) was added to solid phosphine (compound 1) (120.0 mg, 0.372 mmol) and CpRu(CH$_3$CN)$_3$OTf (78.3 mg, 0.179 mmol). Water (16 μL, 0.89 mmol) was added and the resulting solution was stirred for 2 h before being concentrated in vacuo. The residual orange gum was dissolved in acetone (2 mL) containing water (16 μL) and the resulting solution transferred to a tared vial. The vial was placed in a small jar containing hexanes. After 1 d, crystals of 2 had formed and the supernatant was removed from them by pipet. The crystals were rinsed with hexanes and placed under vacuum, leaving orange crystals and powder (172.2 mg, 98% yield). $^1$H NMR (CDCl$_3$, 500 MHz) δ9.24 (br s, 2H), 7.42–7.48 (m), 7.22–7.30 (m), 7.02–7.08 (br m, 4H), 6.80–6.88 (m, 4H), 6.84 (s, 2H, Im-H), 4.07 (s, 5H, Cp-H), 2.75 (s, 6H, N—CH$_3$), 1.33 [s, 18H, C(CH$_3$)$_3$]; $^1$H NMR (acetone-d$_6$, 500 MHz) δ9.12 (sl br s, 2H), 7.54–7.58 (m, 4H), 7.49–7.54 (m, 2H), 7.32–7.41 (m, 6H), 7.17 (s, 2H), 7.13 (sl br t, J=7.5 Hz, 4H), 7.01 (sl br dd, J=8.5, 10 Hz, 4H), 4.19 (s, 5H), 2.85 (s, 6H), 1.36 ppm (s, 18H); $^{13}$C{$^1$H} NMR (CDCl$_3$, 125.7 MHz) δ152.50 (d, J=12.3 Hz), 143.20 (d, J=50.7 Hz), 133.71 (d, J=20.3 Hz), 132.14 (d, J=41.9 Hz), 131.04 (d, J=11.1 Hz), 130.6 (br s), 130.50 (s), 129.96 (s), 129.12 (d, J=10.1 Hz), 128.82 (d, J=9.7 Hz), 128.52 (d, J=7.4 Hz), 120.74 (s), 81.67 (t, J=2.3 Hz), 35.28 (s), 31.96 (s), 30.23 (s) ppm; $^{13}$C{$^1$H} NMR and gHMBC (acetone-d$_6$, 125.7 MHz) δ152.83 (d, J=12.5 Hz, imidazole C-4), 144.35 (d, J=51.4 Hz, imidazole C-2), 132.17 (d, J=11.3 Hz), 131.76 (d, J=10.0 Hz), 131.06 (s), 130.52 (s), 129.81 (d, J=10.0 Hz), 129.55 (d, J=9.4 Hz), 121.84 (d, J=3.5 Hz, imidazole C-3), 82.49 (t, J=2.3 Hz, C$_5$H$_5$), 35.59 (s, NCH$_3$), 32.54 [s, C(CH$_3$)$_3$], 30.61 ppm [s, C(CH$_3$)$_3$]. $^{31}$P{$^1$H} NMR (CDCl$_3$, 80.95 MHz) δ26.72 ppm (br s). Calcd. for C$_{46}$H$_{53}$F$_3$N$_4$O$_4$P$_2$RuS (978.03): C, 56.49; H, 5.46; N, 5.73. Found: C, 56.39; H, 5.21; N, 5.79.

Example 58. Conversion of 4-phenyl-1-butyne to 4-phenylbutanal (Table 1, entry 2)

In the glovebox, to a vial was added catalyst 2 (9.8 mg, 0.010 mmol) and internal standard (Me$_3$Si)$_4$C (0.5 mg). Using portions of acetone-d$_6$ (total volume 0.7 mL), the solid complex and standard were transferred by pipet to a resealable NMR tube. Not all of 2 had dissolved at this point, so the transfer using solvent was partially mechanical. Water (45 μL, 2.5 mmol) was added, followed by PhCH$_2$CH$_2$CCH (64.6 mg, 0.496 mmol) and enough acetone-d$_6$ to bring the total volume to 1.0 mL. The tube was sealed, removed from the glovebox, and briefly placed in a sonicating bath to dissolve all the catalyst to form a pale orange-yellow solution. The $^1$H NMR spectrum of the resulting solution was observed at this point and at intervals during heating of the NMR tube, using the same conditions, in this case on a Varian 500 MHz spectrometer using four 30° pulses and 120 sec delays between pulses. Reaction progress was monitored over time by 1H NMR using an internal standard and measuring signals for catalyst, alkyne, aldehyde and by-product ketone. The results are summarized in Table 1.

The peaks assigned to alkyne in reaction mixture are: $^1$H NMR (500 MHz) δ7.23–7.30 (m, 4H), 7.16–7.21 (m, 1H), 2.79 (t, J=7.5 Hz, 2H, PhCH$_2$CH$_2$CCH), 2.45 (dt, J=1.5, 7.5 Hz, PhCH$_2$CH$_2$CCH), 2.33 ppm (t, J=1.5 Hz, 2H, PhCH$_2$CH$_2$CCH). For aldehyde in reaction mixture: $^1$H NMR (500 MHz) δ9.71 (t, J=1.5 Hz, 1H, CHO), 7.24–7.29 (m, 2H), 7.14–7.22 (m, 3H), 2.63 (~t, J=7.7 Hz, 2H), 2.45 (dt, J=1.5, 7.3 Hz, 2H), 1.90 ppm (tt, J=7.3, 7.7 Hz, 2H); $^{13}$C{$^1$H} NMR (125.7 MHz) δ203.08 (CHO), 142.65 (ipso C), 129.27 and 129.21 (o and m C), 126.75 (p C), 43.67, 35.67, 24.61 ppm.

Example 59. Hydration of 1-hexyne (Table 1, entry 1)

The reaction was performed as described above in Example 58 but using 9.8 mg 2, 0.5 mg (Me$_3$Si)$_4$C, 40.0 mg (0.487 mmol) alkyne, 1.0 mL acetone-d$_6$. For alkyne in the mixture: partial $^1$H NMR δ2.28 (t, J=2.5 Hz, 1H), 2.15 (dt, J=2.5, 7.0 Hz, 2H), 1.35–1.48 (m, 4H). For the aldehyde in the reaction mixture $^1$H NMR δ9.71 (t, J=1.5 Hz, 1H), 2.41 (dt, J=1.5, 7.2 Hz, 2H), 1.58 (~quintet, J=ca. 7 Hz, 2H), 1.25–1.33 (m, 4H).

Gratifyingly, 2 mol % of complex 2 catalyzed the clean conversion of 1-hexyne (Table 1, entry 1) to hexanal in the presence of 5 equiv of water at temperatures near 70° C. in acetone solvent. Within 1.5 d, consumption of alkyne was complete, and 96% of hexanal had been formed. No peaks for the Markovnikov product 2-hexanone were obvious, but to verify this result, approximately 1% of an authentic sample was added. A very small peak increased in size, such that only 0.1% of 2-hexanone had been present before addition of authentic material, meaning that the aldehyde-to-ketone ratio was 1000 to 1. While these conditions were not optimized, they compare favorably with the results of Tokunaga and Wakatsuki with the same alkyne (10% catalyst+30% phosphine, 12 h at 65° C., 71% yield of hexanal, hexanal:2-hexanone=24:1). Moreover, 2 works with a wider variety of substrates than does the Tokunaga-Wakatsuki system, giving much higher selectivities and using much less catalyst.

Example 60. Hydration of 3,3-dimethyl-1-butyne (Table 1, entry 3)

The reaction was carried out as in Example 58 above but using 9.6 mg 2, 0.4 mg (Me$_3$Si)$_4$C, 42.5 mg (0.517 mmol) alkyne, 1.1 mL acetone-d$_6$. For alkyne in the mixture: $^1$H NMR δ2.42 (s, 1H) and 1.19 ppm (s, 9H). For the aldehyde in the reaction mixture $^1$H NMR δ9.79 (t, J=1.5 Hz, 1H), 2.25 (d, J=1.5 Hz, 2H), 1.04 ppm (s, 9H).

Example 61. Hydration of phenylethyne (Table 1, entry 4)

The reaction was performed as in Example 58 but using 9.9 mg 2 (0.101 mmol), 0.5 mg (Me$_3$Si)$_4$C, 50.9 mg (0.498 mmol) alkyne, 1.0 mL acetone-d$_6$. For alkyne in the mixture: partial $^1$H NMR δ7.32–7.41 (m, 3H), 3.31 ppm (s, 1H). For the aldehyde in the reaction mixture partial $^1$H NMR δ9.72 (t, J=2.0 Hz, 1H), 3.73 ppm (d, J=2.0 Hz, 2H).

Example 62. Hydration of TBSOCH$_2$CCH (Table 1, entry 5)

The reaction was conducted as in Example 58 but using 9.8 mg 2 (0.0101 mmol), 0.5 mg TMS$_4$C, 85.6 mg (0.503 mmol) alkyne, 1.0 mL acetone-d$_6$. For alkyne in the mixture: $^1$H NMR δ4.31 (d, J=2.5 Hz, 2H), 2.86 (t, J=2.5 Hz, 1H), 0.89 (s, 9H), 0.11 ppm (s, 6H). For the aldehyde in the reaction: $^1$H NMR δ9.73 (t, J=2.5 Hz, 1H), 4.01 (t, J=6.0 Hz, 2H), 2.57 (dt, J=2.5, 6.0 Hz, 2H), 0.87 (s, 9H), 0.06 ppm (s, 6H).

Example 63. Hydration of THPOCH$_2$CCH (Table 1, entry 6)

This reaction was performed as in Example 58 above but using 9.6 mg 2 (0.0098 mmol), 1.0 mg (Me$_3$Si)$_4$C, 68.3 mg (0.487 mmol) alkyne, 1.0 mL acetone-d$_6$. For alkyne in the mixture: $^1$H NMR δ4.77 [t, J=3.2 Hz, 1H, CH(OR)$_2$], 4.23 (dd, J=2.5, 16 Hz, 1H), 4.18 (dd, J=2.5, 16 Hz, 1H), 3.76 (ddd, J=2.5), 3.44–3.49 (m, 1H), 2.89 (t, J=2.5 Hz, 1H), 1.70–1.80 (m, 1 H), 1.61–1.70 (m, 1H), 1.42–1.59 ppm (m, 4H). $^1$H NMR spectrum of aldehyde in reaction mixture: δ9.73 (t, J=1.8 Hz, 1H), 4.60 (t, J=3.5 Hz, 1H), 4.03 (td, J=6.1, 10.3 Hz, 1H), 3.78 (ddd, J=3.3, 8.6, 11.3 Hz, 1H), 3.72 (td, J=6.0, 10.3 Hz, 1H), 3.42–3.48 (m, 1H), 2.64 (dt, J=2.0, 6.0 Hz, 2H), 1.68–1.76 (m, 1H), 1.57–1.65 (m, 1H), 1.40–1.55 ppm (m, 4H).

Example 64. Control experiments

Several control experiments are summarized in Table 1 and show that the imidazole groups are essential for successful catalysis. First, in hydration of 1-hexyne, simple triarylphosphine ligands PPh$_3$ and P(4-ClC$_6$H$_4$)$_3$ on the CpRu$^+$ cation give less than 0.5% yields of hexanal, with no 2-hexanone being detected. The latter phosphine was examined as a model for the mild electron-withdrawing character of the imidazole ring compared with phenyl. The electronic effect of the imidazole substituent was probed by making trans-Rh(Cl)(CO)(L)$_2$ using the N-isopropyl analog of 1 as phosphine ligand L (unpublished results). Furthermore, if the imidazole groups function simply as a base, their placement in 2 is crucial: addition of 2 mol of either the hindered imidazole base 5 or Et$_3$N to mixtures containing 4 led to virtually no production of aldehyde.

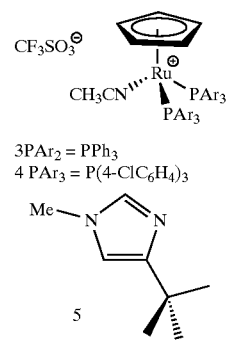

3PAr$_2$ = PPh$_3$
4 PAr$_3$ = P(4-ClC$_6$H$_4$)$_3$

TABLE 1

Efficient and selective catalysis[a]

| | | | Aldehyde yield (%) | | | | |
|---|---|---|---|---|---|---|---|
| Entry | Cat. | Substitutent R | 1 h | 3 h | 21 h | Later or w/ more cat. | Aldehyde:Ketone Ratio[b] |
| 1 | 2 | CH₃CH₂CH₂CH₂ | 19 | 39 | 92 | 96% after 36 h | 1000:1 |
| 2 | | C₆H₅CH₂CH₂ | 19 | 40 | 88 | 92% after 46 h | 150:1 |
| 3 | | (CH₃)₃C | 1.4 | 3.5 | 21 | 91%[c] | ≧130:1 |
| 4 | | C₆H₅ | 4.5 | 9.6 | 20 | 54%[d] | 135:1 |
| 5 | | t-BuMe₂SiO-CH₂- | 12 | 28 | 91 | 96% after 36 h | ≧200:1 |
| 6 | | tetrahydropyranyl-O-CH₂- | 16 | 35 | 83 | 86% after 50 h | ≧400:1 |
| 7 | 3 | CH₃CH₂CH₂CH₂ | 0 | 0.1 | 0.3 | | |
| 8 | 4 | CH₃CH₂CH₂CH₂ | 0.2 | 0.3 | 0.5 | | |
| 9 | 4 + 2 5 | CH₃CH₂CH₂CH₂ | 0 | <0.1 | <0.1 | | |
| 10 | 4 + 2 Et₃N | CH₃CH₂CH₂CH₂ | 0 | 0 | 0 | | |

[a]Conditions: 0.5 mmol alkyne, 5 equiv water, 2 mol % catalyst and (Me₃Si)₄C internal standard in acetone-d₆ (1 mL) heated in a sealed NMR tube in an oil bath (67–72° C.). Yields and products identified by ¹H and in some cases ¹³C NMR data.
[b]Authentic sample of ketone added at end of reaction period.
[c]49% after 68 h; 91% after additional 108 h at 88–91° C.
[d]54% after three additions of 2 mol % 2 and 36–45 h heating each time.

Although the present invention has been described with respect to various specific examples and embodiments, it is to be understood that the invention is not limited thereto and that it can be variously practiced within the scope of the following claims.

What is claimed is:

1. An organic compound selected from the group consisting of:

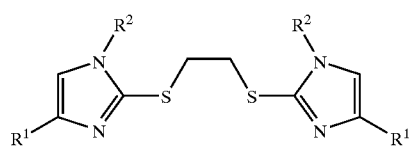

4 a R$^1$ = t-Bu, R$^2$ = Me
b R$^1$ = t-Bu, R$^2$ = i-Pr

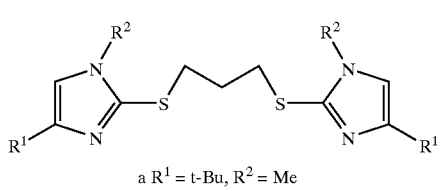

5 a R$^1$ = t-Bu, R$^2$ = Me

-continued

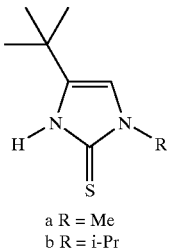

1 a R = Me
b R = i-Pr

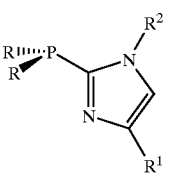

9 a R$^1$ = t-Bu, R$^2$ = Me, R = Ph
b R$^1$ = t-Bu, R$^2$ = i-Pr, R = Ph
c R$^1$ = t-Bu, R$^2$ = i-Pr, R = t-Bu
d R$^1$ = t-Bu, R$^2$ = Me, R = Me

-continued

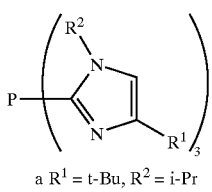

a R¹ = t-Bu, R² = i-Pr

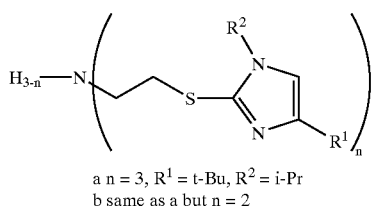

a n = 3, R¹ = t-Bu, R² = i-Pr
b same as a but n = 2

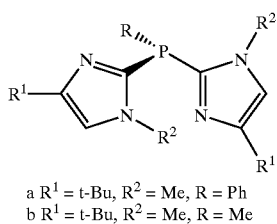

a R¹ = t-Bu, R² = Me, R = Ph
b R¹ = t-Bu, R² = Me, R = Me

2. A transition metal complex comprising:
(a) a transition metal selected from the group consisting of Cr, Mn, Fe, Co, Ni, Cu, Zn, Zr, Nb, Mo, Ru, Rh, Pd, Ag, Hf, Ta, W, Re, Os, Ir, Pt, and Au; and
(b) at least one organic ligand coordinated to said transition metal, wherein said at least one organic ligand contains (i) at least two different heteroatoms selected from the group consisting of N, P, and S, and (ii) at least one substituted or unsubstituted imidazole group, wherein said complex is effective in converting a terminal alkyne to an aldehyde in the presence of water at or near neutral pH.

3. The transition metal complex of claim 2, which is capable of chemically coordinating to a water molecule at ambient temperature and pressure.

4. The transition metal complex of claim 2, wherein an N atom of said at least one imidazole group is separated from said different type of heteroatom by at least one atom.

5. The transition metal complex of claim 2, wherein said two different heteroatoms are P and N.

6. The transition metal complex of claim 2, wherein one of said two different heteroatoms binds to the transition metal and the at least one imidazole group does not bind to the transition metal.

7. The transition metal complex of claim 2, wherein the transition metal is Ru.

8. A method of converting a terminal alkyne to an aldehyde comprising:
contacting the alkyne with a transition metal complex in the presence of water to form a reaction admixture thereof, wherein the transition metal complex contains at least one organic ligand including at least two different heteroatoms selected from N, P, and S, and at least one substituted or unsubstituted imidazole group; and
subjecting the reaction admixture to reaction conditions effective to convert the alkyne to the aldehyde, thereby converting a terminal alkyne to an aldehyde wherein an end of the terminal alkyne is attached to a monovalent radical.

9. The method of claim 8, wherein the transition metal complex catalytically converts alkyne to aldehyde.

10. The method of claim 8, wherein the subjecting occurs at or about neutral pH.

11. The method of claim 8, wherein the two different heteroatoms act cooperatively in the transition metal complex to effect the conversion.

12. The method of claim 8, wherein the two different heteroatoms are P and N.

13. A transition metal complex comprising:
(a) a transition metal selected from the group consisting of Cr, Mn, Fe, Co, Ni, Cu, Zn, Zr, Nb, Mo, Ru, Rh, Pd, Ag, Hf, Ta, W, Re, Os, Ir, Pt, and Au; and
(b) at least one organic ligand coordinated to said transition metal, wherein said at least one organic ligand is selected from the group consisting of:

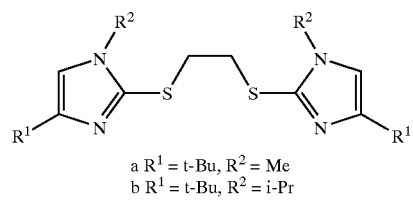

a R¹ = t-Bu, R² = Me
b R¹ = t-Bu, R² = i-Pr

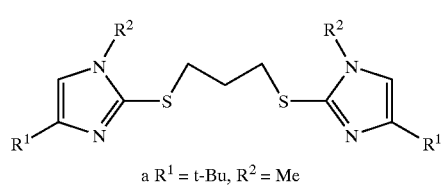

a R¹ = t-Bu, R² = Me

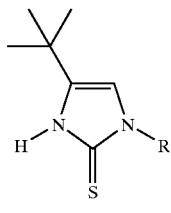

a R = Me
b R = i-Pr

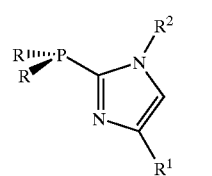

a R¹ = t-Bu, R² = Me, R = Ph
b R¹ = t-Bu, R² = i-Pr, R = Ph
c R¹ = t-Bu, R² = i-Pr, R = t-Bu
d R¹ = t-Bu, R² = Me, R = Me

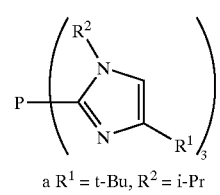

a R¹ = t-Bu, R² = i-Pr

-continued

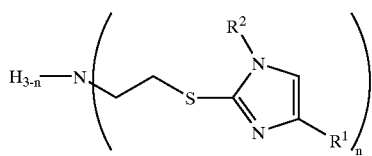

a n = 3, R¹ = t-Bu, R² = i-Pr
b same as a but n = 2

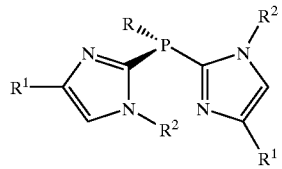

a R¹ = t-Bu, R² = Me, R = Ph
b R¹ = t-Bu, R² = Me, R = Me

14. The transition metal complex of claim 13, wherein said complex is effective in converting a terminal alkyne to an aldehyde in the presence of water at or near neutral pH.

15. The transition metal complex of claim 13, which is capable of chemically coordinating to a water molecule at ambient temperature and pressure.

16. The transition metal complex of claim 13, wherein a heteroatom of the ligand binds to the transition metal and a N heterocycle of the ligand does not bind to the transition metal.

17. The transition metal complex of claim 13, wherein the transition metal is Ru.

* * * * *